United States Patent
Yamashita

[11] 4,111,529
[45] Sep. 5, 1978

[54] OPTICAL SYSTEM FOR AN ENDOSCOPE

[75] Inventor: Nobuo Yamashita, Tama, Japan

[73] Assignee: Olympus Optical Co., Ltd., Japan

[21] Appl. No.: 777,442

[22] Filed: Mar. 14, 1977

Related U.S. Application Data

[63] Continuation of Ser. No. 602,312, Aug. 6, 1975, abandoned.

[30] Foreign Application Priority Data

Aug. 14, 1974 [JP] Japan .................... 74/92308

[51] Int. Cl.² .......................... A61B 1/06; G02B 9/12
[52] U.S. Cl. ........................ 350/225; 128/6; 350/208
[58] Field of Search ............. 128/6, 7, 8, 9, 4, 5; 350/96 BC, 225, 208

[56] References Cited

U.S. PATENT DOCUMENTS

| | | | |
|---|---|---|---|
| 1,085,868 | 2/1914 | König | 350/225 |
| 1,680,490 | 8/1928 | Wappler | 128/7 |
| 2,182,390 | 12/1939 | Reardon | 128/6 |
| 2,224,464 | 12/1940 | Wolf | 128/6 X |
| 2,363,701 | 11/1944 | Soetbeer | 128/6 X |
| 2,519,760 | 8/1950 | Hett | 128/8 X |
| 2,772,601 | 12/1956 | Bertele | 350/225 X |
| 2,927,574 | 3/1960 | Scholz | 128/6 |
| 2,987,960 | 6/1961 | Sheldon | 350/96 BC UX |
| 3,279,460 | 10/1966 | Sheldon | 350/96 BC X |
| 3,637,282 | 1/1972 | Hayamizu et al. | 350/175 TS X |
| 3,871,365 | 3/1975 | Chikama | 128/5 |

FOREIGN PATENT DOCUMENTS

| | | | |
|---|---|---|---|
| 677,592 | 6/1939 | Fed. Rep. of Germany | 350/225 |
| 1,257,012 | 12/1971 | United Kingdom | 350/96 BC |
| 1,157,932 | 7/1969 | United Kingdom | 128/6 |

*Primary Examiner*—Clifford D. Crowder
*Attorney, Agent, or Firm*—Cushman, Darby & Cushman

[57] ABSTRACT

An optical system for an endoscope having the optical axis of an objective parallely shifted from the center line of an image fiber so that the center of the field of observation of the objective coincides with the position of a forceps means or with the center of the field of illumination of a light guide. The objective comprises first, second and third lens components wherein the first is a negative singlet, the second a positive singlet meniscus and the third a cemented positive doublet and wherein the stop is between the first and second components.

1 Claim, 5 Drawing Figures

OPTICAL SYSTEM FOR AN ENDOSCOPE

This applicaton is a continuation of Ser. No. 602,312, filed Aug. 6, 1975, now abandoned.

BACKGROUND OF THE INVENTION a. Field of the Invention

The present invention relates to an optical system for an endoscope and, more particularly, to an optical system for an endoscope for which the optical axis of the objective is slightly shifted in parallel with the center line of the image fiber.

b. Description of the prior art

As known widely, an endoscope is used for observing the inner wall etc. of a body cavity such as a stomachs by inserting into the body cavity. Besides, as it is necessary to cut off the affected part by using a forceps means while observing by means of the endoscope, endoscopes are generally provided with forceps means for cutting off the affected part. As, however, the position of said forceps means is considerably distant from the optical axis of the optical system of the endoscope, known endoscopes have a disadvantage that it is difficult to observe the position of the forceps means when cutting the affected part by the forceps means while observing the affected part. To eliminate the above-mentioned disadvantage, known optical systems for endoscopes are provided with a prism or reflecting mirrors in front of the objective as shown in FIG. 1 and FIG. 2. In the example shown in FIG. 1, a prism 3 is provided in front of the optical system for endoscopes which comprises an image fiber 1 for transmitting the image of the object and objective 2. By utilizing refraction of said prism 3, the forceps means is put to a position near the center of the field of the optical system. In the example shown in FIG. 2, a prism 4 is provided in front of the objective 2. By means of reflection by reflecting surfaces 4a and 4b of said prism 4, the forceps means is put to a position near the center of the field. (In the latter case, it is of course all right to provide two reflecting mirrors, which are combined to each other, instead of said prism 4.)

The above-mentioned known means, however, have the following disadvantages. In case of the former example shown in FIG. 1, astigmatism is caused and, moreover, shifting of the image for different wavelengths is caused by dispersion of the prism. Furthermore, when it is attempted to make the field angle of the optical system wide, it is necessary to make the prism 3 large and, therefore, the distal end of the endoscope becomes also large when such large prism is provided in the distal end. In case of the latter example shown in FIG. 2, two reflecting surfaces exist and the optical axis is deflected by said reflecting surfaces. Consequently, the distal end becomes large and, moreover, flare tends to occur.

SUMMARY OF THE INVENTION

It is, therefore, a primary object of the present invention to provide an optical system for an endoscope having the optical axis of the objective slightly shifted from the center line the image fiber.

DETAILED DESCRIPTION OF THE PREFERRED EMBODIMENTS

Figure 1:
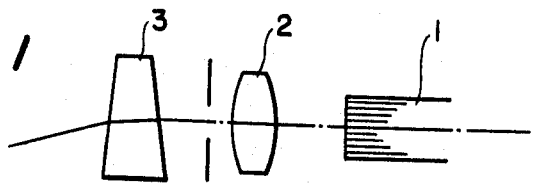
FIGS. 1 and 2 respectively show examples of known optical systems for microscopes.
Figure 2:
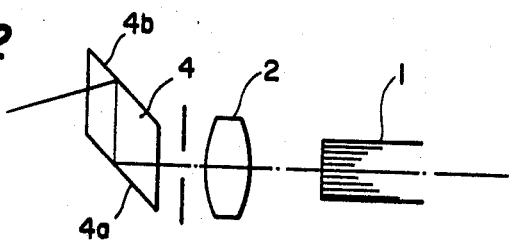
Figure 3:
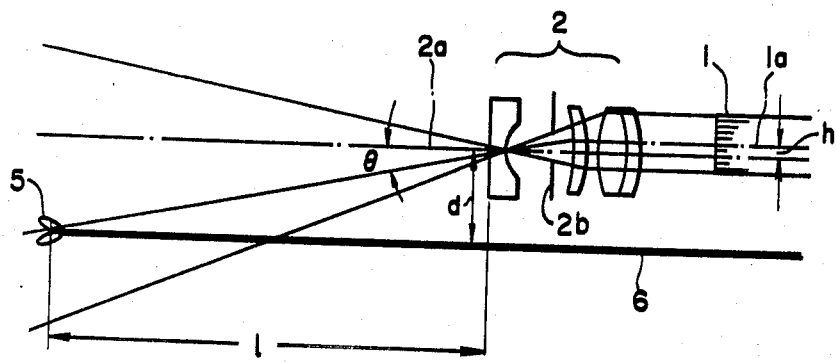
FIG. 3 shows a sectional view of an embodiment of the present invention.

In the following, contents of the present invention are described in detail referring to the accompanying drawings. In FIG. 3, Numerals 1 and 2 respectively designate an image fiber and objective as in the cases of the aforementioned examples of known means. Numeral 1a designates the center line of said image fiber 1 and numeral 2a designates the optical axis of said objective 2. The objective 2 comprises a negative lens, positive lens and cemented positive doublet and the stop 2b is arranged between the negative lens and positive lens. Numeral 5 designates a forceps means and numeral 6 designates a wire for operating said forceps means 5. When, referring to FIG. 3, reference symbol $l$ represents the distance of the forceps means 5 from the front surface of the objective 2 and reference symbol $d$ represents the distance from the optical axis 2a of the objective to the wire 6, the angle of incidence $\theta$ of the ray from the forceps means 5 to the objective 2 is expressed by the following formula.

$$\tan \theta = d/l \qquad (1)$$

On the other hand, height of ray $h$ of the ray entered the objective at the angle of incidence $\theta$ (i.e., the distance between the center line 1a of the image fiber and optical axis 2a of the objective) is expressed by the following formula where reference symbol $f$ represents the focal length of the objective 2.

$$h = f \tan \theta \qquad (2)$$

Therefore, the following formula (3) is obtained from the formulas (1) and (2).

$$h = d/l f \qquad (3)$$

Therefore, the forceps means at the above-mentioned position, i.e., at the distance $l$ from the front surface of the objective and at the distance $d$ from the optical axis of the objective, can be put to the center of the field of observation when the optical axis 2a of the objective 2 is shifted from the center line 1a of the optical fiber by the value of $h$(amount of shifting) obtained by the above formula (3).

Figure 4:
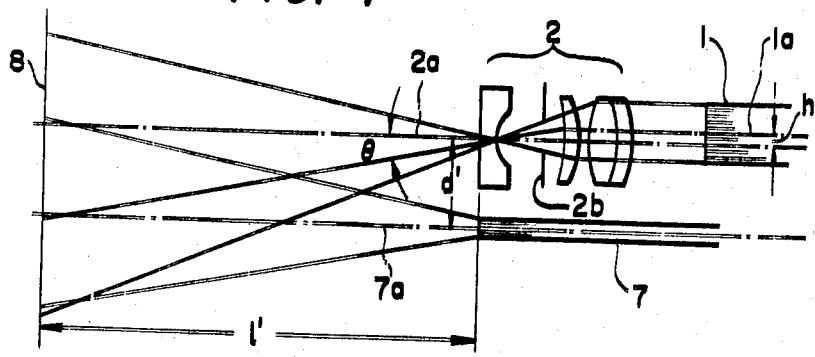
FIG. 4 shows a sectional view of another embodiment of the present invention.

In case of an endoscope having an illuminating system provided by the side of the image fiber, the area illuminated by the illuminating system becomes different from the area observed through the objective. FIG. 4 shows an embodiment in which the present invention is applied to the above-mentioned case.

In FIG. 4, numeral 7 designates a light guide used for illuminating and numeral 8 designates the surface of the object to be observed. When reference symbol $d'$ represents the distance between the center line 7a of the light guide 7 and optical axis 2a of the objective and reference symbol $l'$ represents the distance from the object surface 8 to the front surface of the objective 2, the distance $h$ between the center line 1a of the image fiber 1 and optional axis 2a of the objective 2 is expressed by the following formula in the same way as described before.

$$h = (d'/l')f \qquad (3')$$

Figure 5:
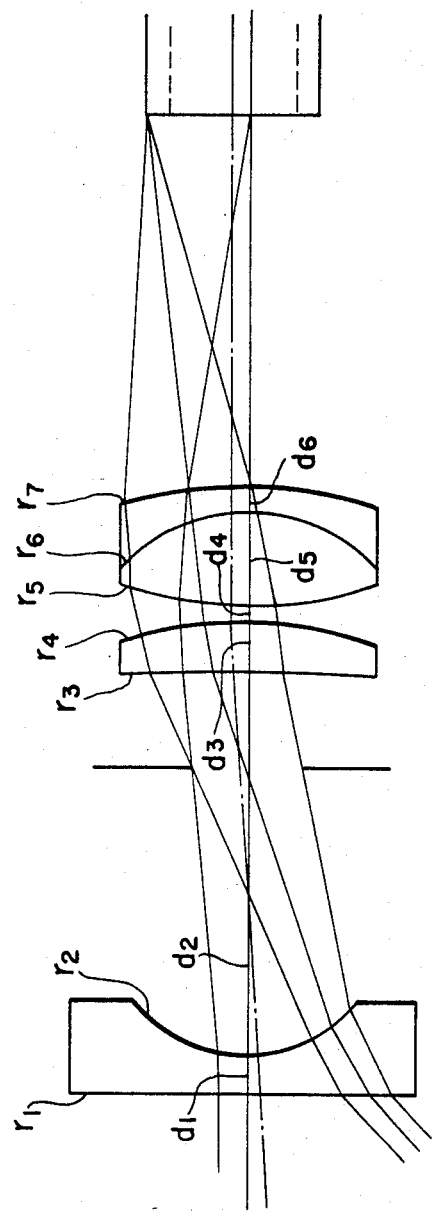
FIG. 5 shows a sectional view especially illustrating the objective of the optical system according to the present invention in detail.

Now, an example of numerical values of the objective to be used in the above-mentioned optical system for an endoscope according to the present invention is given below referring to the optical system shown in FIG. 5.

| | | | |
|---|---|---|---|
| $r_1 = \infty$ | | | |
| | $d_1 = 0.6$ | $n_1 = 1.51633$ | $\nu_1 = 64.1$ |
| $r_2 = 2.175$ | | | |
| | $d_2 = 6.49$ | | |
| $r_3 = -49.125$ | | | |
| | $d_3 = 1.0$ | $n_2 = 1.69680$ | $\nu_2 = 55.7$ |
| $r_4 = -6.007$ | | | |
| | $d_4 = 0.2$ | | |
| $r_5 = 7.42$ | | | |
| | $d_5 = 1.6$ | $n_3 = 1.62041$ | $\nu_3 = 60.3$ |
| $r_6 = -3.187$ | | | |
| | $d_6 = 0.5$ | $n_4 = 1.84666$ | $\nu_4 = 23.9$ |
| $r_7 = -6.888$ | | | |
| $f = 2.5,$ | F 1 : 3 | | | wherein reference symbols $r_1$ through $r_7$ respectively represent radii of curvature of respective surfaces of respective lenses, reference symbols $d_1$ through $d_6$ respectively represent thicknesses of respective lenses and airspaces between respective lenses, reference symbols $n_1$ through $n_4$ respectively represent refractive indices of respective lenses, and reference symbols $\nu_1$ through $\nu_4$ respectively represent Abbe's numbers of respective lenses.

The objective having the above numerical values is designed on the basis of $\theta = 7°$. Therefore, $\tan \theta = 0.123$ and the focal length $f$ of the objective 2 is 2.5 and, consequently, the amount of shifting $h$ is $h = (d/l)f = 0.3$. As said amount of shifting is very small as above, the optical system and the distal end of the endoscope accommodating said optical system do not become large even when the optical axis of the objective is shifted from the center line of the image fiber. Besides, when the objective is designed based on the angle including the above-mentioned amount of shifting $h$, no unfavourable influence is caused on the quality of the image.

As described in the above, by the optical system for an endoscope according to the present invention, it is possible to observe by putting the forceps means near the center of the field only by slightly shifting the optical axis of the objective from the center line of the image fiber and it is not necessary to provide a prism, reflecting mirrors, etc. in front of the objective. Therefore, the endoscope does not become large in size as in the case when the prism or the like is provided and, moreover, it is possible to obtain a favourable image for observation.

I claim:

1. An optical system for an endoscope comprising an image fiber for transmitting an image of an object to be observed and an objective arranged adjacent to one end face of said image fiber in order to form an image of the object on said end face of said image fiber, said objective comprising a first, second and third lens component, said first lens component being a negative singlet lens, said second lens component being a positive singlet meniscus lens, and said third lens component being a cemented positive doublet lens, the stop of said optical system for an endoscope being arranged between said first lens component and said second lens component, the optical axis of said objective being parallely shifted from the center line of said image fiber, in which said objective has numerical values as given below:

| | | | |
|---|---|---|---|
| $r_1 = \infty$ | | | |
| | $d_1 = 0.6$ | $n_1 = 1.51633$ | $\nu_1 = 64.1$ |
| $r_2 = 2.175$ | | | |
| | $d_2 = 6.49$ | | |
| $r_3 = -49.125$ | | | |
| | $d_3 = 1.0$ | $n_2 = 1.69680$ | $\nu_2 = 55.7$ |
| $r_4 = -6.007$ | | | |
| | $d_4 = 0.2$ | | |
| $r_5 = 7.42$ | | | |
| | $d_5 = 1.6$ | $n_3 = 1.62041$ | $\nu_3 = 60.3$ |
| $r_6 = -3.187$ | | | |
| | $d_6 = 0.5$ | $n_4 = 1.84666$ | $\nu_5 = 23.9$ |
| $r_7 = -6.888$ | | | |
| | $f = 2.5$ | F 1 : 3 | | wherein reference symbols $r_1$ through $r_7$ respectively represent radii of curvature of respective surfaces of respective lenses, reference symbols $d_1$ through $d_6$ respectively represent thicknesses of respective lenses and airspaces between respective lenses, reference symbols $n_1$ through $n_4$ respectively represent refractive indices of respective lenses, and reference symbols $\nu_1$ through $\nu_4$ respectively represent Abbe's numbers of repective lenses.

* * * * *